United States Patent
Larsen et al.

(10) Patent No.: US 9,095,660 B2
(45) Date of Patent: Aug. 4, 2015

(54) DISPOSABLE DOUBLE POINT INJECTION NEEDLE AND AN INSULIN INJECTION SYSTEM COMPRISING A DISPOSABLE DOUBLE POINT INJECTION NEEDLE

(75) Inventors: Carsten Gerner Larsen, Kgs. Lyngby (DK); Lars Stenholt, Humlebaek (DK); Anders Molin, Kobenhavn K. (DK); Jorn Rex, Roskilde (DK); Bjorn Gullak Larsen, Bagsvaerd (DK)

(73) Assignee: Novo Nordisk A/S, Bagsvaerd (DK)

( * ) Notice: Subject to any disclaimer, the term of this patent is extended or adjusted under 35 U.S.C. 154(b) by 511 days.

(21) Appl. No.: 13/278,769

(22) Filed: Oct. 21, 2011

(65) Prior Publication Data

US 2012/0277724 A1   Nov. 1, 2012

Related U.S. Application Data

(63) Continuation of application No. 11/097,414, filed on Apr. 1, 2005, now Pat. No. 8,075,522, which is a (Continued)

(30) Foreign Application Priority Data

May 31, 2000   (EP) ..................................... 00610052
Nov. 28, 2000   (DK) ........................... PA 2000 01790

(51) Int. Cl.
   *A61M 5/32*   (2006.01)
   *A61M 5/24*   (2006.01)
   *A61M 5/34*   (2006.01)

(52) U.S. Cl.
   CPC ............. *A61M 5/3272* (2013.01); *A61M 5/326* (2013.01); *A61M 5/24* (2013.01); *A61M 5/3257* (2013.01);

(Continued)

(58) Field of Classification Search
   CPC ... A61M 5/322; A61M 5/3234; A61M 5/508; A61M 5/5013; A61M 5/3202; A61M 5/3213; A61M 5/3216; A61M 5/3243; A61M 5/326; A61M 2005/3231; A61M 2005/3224; A61M 5/5086; A61M 5/3134; A61M 2005/3104; A61M 39/1011; A61M 5/3129; A61M 5/24; A61M 5/31511; A61M 2005/3139; A61M 5/3135; A61M 5/3271; A61M 2005/3247; A61M 5/3257; A61M 5/31525; A61M 5/31553; A61M 5/31535; A61M 5/3158; A61M 5/31513; A61M 5/14566; A61M 5/31515; A61M 3/00; A61M 5/3272; A61M 2005/3267; A61M 2005/583
   IPC .................................................... A61M 5/3272
   See application file for complete search history.

(56) References Cited

U.S. PATENT DOCUMENTS 3,021,942 A   2/1962   Hamilton
(Continued)

FOREIGN PATENT DOCUMENTS

DE   100 09 814   9/2001
(Continued)

OTHER PUBLICATIONS

Notice of Opposition to European Patent 1289587 Dated May 3, 2006.
(Continued)

*Primary Examiner* — Manuel Mendez
(74) *Attorney, Agent, or Firm* — Wesley Nicolas (57) ABSTRACT

A disposable double pointed injection needle has a needle hub to which a thin needle cannula is permanently fastened and which needle hub can be mounted on to a syringe comprising a dose setting and injection mechanism and a cartridge containing a liquid medicine to be injected subcutaneously into a human body. The needle hub is provided with a safety shield guided on the needle hub. The safety shield is urged in a direction away from the needle hub by a spring located between the needle hub and the safety shield. After injection the shield is moved away from the needle hub by the spring and locked in an irreversible position where the safety shield covers the needle cannula and prevents accidental needle stick injuries.

4 Claims, 5 Drawing Sheets

Related U.S. Application Data continuation of application No. 10/379,021, filed on Mar. 4, 2003, now abandoned, which is a continuation of application No. 09/870,276, filed on May 30, 2001, now Pat. No. 6,547,764.

(60) Provisional application No. 60/254,051, filed on Dec. 7, 2000.

(52) U.S. Cl.
CPC ............... *A61M 5/347* (2013.01); *A61M 5/349* (2013.01); *A61M 2005/3267* (2013.01); *A61M 2205/583* (2013.01); *A61M 2205/59* (2013.01)

(56) References Cited

U.S. PATENT DOCUMENTS

| | | | |
|---|---|---|---|
| 3,114,455 A | 12/1963 | Claisse et al. | |
| 3,390,759 A | 7/1968 | Vanderbeck | |
| 3,916,893 A | 11/1975 | De Felice | |
| 4,244,378 A | 1/1981 | Brignola | |
| 4,248,246 A | 2/1981 | Ikeda | |
| 4,592,745 A * | 6/1986 | Rex et al. | 604/211 |
| 4,723,943 A | 2/1988 | Spencer | |
| 4,767,413 A | 8/1988 | Haber et al. | |
| 4,795,432 A | 1/1989 | Karczmer | |
| 4,810,248 A | 3/1989 | Masters et al. | |
| 4,813,940 A | 3/1989 | Parry | |
| 4,863,436 A | 9/1989 | Glick | |
| 4,894,055 A | 1/1990 | Sudnak | |
| 4,915,701 A | 4/1990 | Halkyard | |
| 5,002,536 A | 3/1991 | Thompson et al. | |
| 5,053,018 A | 10/1991 | Talonn et al. | |
| 5,104,386 A | 4/1992 | Alzain | |
| 5,169,392 A | 12/1992 | Ranford et al. | |
| 5,188,599 A | 2/1993 | Botich et al. | |
| 5,188,614 A * | 2/1993 | Hart | 604/197 |
| 5,195,985 A | 3/1993 | Hall | |
| 5,197,322 A | 3/1993 | Indravudh | |
| 5,197,953 A * | 3/1993 | Colonna | 604/110 |
| 5,201,708 A | 4/1993 | Martin | |
| 5,201,721 A | 4/1993 | Lee et al. | |
| 5,211,628 A * | 5/1993 | Marshall | 604/110 |
| 5,242,401 A | 9/1993 | Colsky | |
| 5,250,031 A * | 10/1993 | Kaplan et al. | 604/110 |
| 5,250,037 A | 10/1993 | Bitdinger | |
| 5,267,961 A | 12/1993 | Shaw | |
| 5,292,314 A | 3/1994 | D'Alessio et al. | |
| 5,295,975 A | 3/1994 | Lockwood, Jr. | |
| D347,894 S | 6/1994 | Hansen et al. | |
| 5,324,264 A | 6/1994 | Whitaker | |
| 5,338,310 A | 8/1994 | Lewandowski | |
| 5,338,311 A | 8/1994 | Mahurkar | |
| 5,346,480 A | 9/1994 | Hess et al. | |
| 5,385,551 A | 1/1995 | Shaw | |
| 5,389,085 A | 2/1995 | D'Alessio et al. | |
| 5,395,339 A | 3/1995 | Talonn et al. | |
| 5,403,286 A | 4/1995 | Lockwood, Jr. | |
| 5,405,362 A | 4/1995 | Kramer et al. | |
| 5,415,645 A | 5/1995 | Friend et al. | |
| 5,417,662 A | 5/1995 | Hjertman et al. | |
| 5,429,612 A | 7/1995 | Berthier | |
| 5,433,712 A | 7/1995 | Stiles et al. | |
| 5,462,535 A | 10/1995 | Bonnichsen | |
| 5,472,430 A | 12/1995 | Vaillancourt | |
| 5,478,316 A | 12/1995 | Bitdinger et al. | |
| 5,486,164 A | 1/1996 | Streck | |
| 5,489,275 A | 2/1996 | Thompson et al. | |
| 5,545,145 A | 8/1996 | Clinton et al. | |
| 5,549,558 A | 8/1996 | Martin | |
| 5,591,138 A | 1/1997 | Vaillancourt | |
| 5,593,390 A | 1/1997 | Castellano et al. | |
| 5,611,785 A | 3/1997 | Mito et al. | |
| 5,613,952 A * | 3/1997 | Pressly et al. | 604/110 |
| 5,626,566 A | 5/1997 | Petersen et al. | |
| 5,634,910 A | 6/1997 | Kanner et al. | |
| 5,674,203 A | 10/1997 | Lewandowski | |
| 5,674,204 A | 10/1997 | Chanoch | |
| 5,681,291 A | 10/1997 | Galli | |
| 5,688,241 A | 11/1997 | Asbaghi | |
| 5,693,027 A | 12/1997 | Hansen et al. | |
| 5,709,662 A | 1/1998 | Olive et al. | |
| 5,746,727 A | 5/1998 | Graves et al. | |
| 5,755,709 A | 5/1998 | Cuppy | |
| 5,769,826 A | 6/1998 | Johnson et al. | |
| 5,795,336 A | 8/1998 | Romano et al. | |
| 5,800,403 A * | 9/1998 | Pressly et al. | 604/195 |
| 5,823,997 A | 10/1998 | Thorne | |
| 5,843,036 A | 12/1998 | Olive et al. | |
| 5,873,462 A | 2/1999 | Ngueyen et al. | |
| 5,873,856 A | 2/1999 | Hjertman et al. | |
| 5,885,249 A | 3/1999 | Irisawa | |
| 5,893,845 A | 4/1999 | Newby et al. | |
| 5,921,964 A | 7/1999 | Martin | |
| 5,931,817 A | 8/1999 | Nguyen et al. | |
| 5,941,857 A | 8/1999 | Ngueyen et al. | |
| 5,944,700 A | 8/1999 | Ngueyen et al. | |
| 5,951,530 A | 9/1999 | Steengaard et al. | |
| 5,961,495 A | 10/1999 | Walters et al. | |
| 5,964,731 A | 10/1999 | Kovelman | |
| 5,968,021 A | 10/1999 | Ejlersen | |
| 5,971,966 A | 10/1999 | Lav | |
| 5,980,491 A | 11/1999 | Hansen | |
| 5,980,494 A | 11/1999 | Malenchek et al. | |
| 5,984,906 A | 11/1999 | Bonnichsen et al. | |
| 6,001,080 A | 12/1999 | Kuracina et al. | |
| 6,001,082 A | 12/1999 | Dair et al. | |
| 6,004,297 A | 12/1999 | Steenfeldt-Jensen et al. | |
| 6,017,329 A | 1/2000 | Hake | |
| 6,077,253 A | 6/2000 | Cosme | |
| 6,110,149 A | 8/2000 | Klitgaard et al. | |
| 6,126,646 A | 10/2000 | Hansen et al. | |
| 6,132,401 A | 10/2000 | Van Der Meyden et al. | |
| 6,162,197 A | 12/2000 | Mohammad | |
| 6,190,361 B1 | 2/2001 | Gettig et al. | |
| 6,203,529 B1 | 3/2001 | Gabriel | |
| 6,319,225 B1 | 11/2001 | Sugita et al. | |
| 6,322,540 B1 | 11/2001 | Grabis et al. | |
| 6,379,337 B1 | 4/2002 | Mohammad | |
| 6,391,003 B1 | 5/2002 | Lesch, Jr. | |
| 6,409,706 B1 | 6/2002 | Loy | |
| 6,419,661 B1 | 7/2002 | Kuhr | |
| 6,436,086 B1 | 8/2002 | Newby et al. | |
| 6,494,865 B1 | 12/2002 | Alchas | |
| 6,547,764 B2 | 4/2003 | Larsen et al. | |
| 6,569,123 B2 | 5/2003 | Alchas et al. | |
| 6,733,465 B1 | 5/2004 | Smutney et al. | |
| 6,773,415 B2 | 8/2004 | Heiniger | |
| 6,885,129 B2 | 4/2005 | Oohashi et al. | |
| 6,986,760 B2 | 1/2006 | Giambattista et al. | |
| 7,074,211 B1 | 7/2006 | Heiniger et al. | |
| 7,314,464 B2 | 1/2008 | Giambattista et al. | |
| 7,553,293 B2 | 6/2009 | Jensen et al. | |
| 7,815,611 B2 | 10/2010 | Giambattista et al. | |
| 8,632,503 B2 | 1/2014 | Ruan et al. | |
| 8,647,307 B2 | 2/2014 | Gratwohl et al. | |
| 2001/0049506 A1 | 12/2001 | Schoenfeld et al. | |
| 2002/0004648 A1 | 1/2002 | Larsen et al. | |
| 2003/0093035 A1 | 5/2003 | Mohammed | |
| 2003/0137905 A1 | 7/2003 | Emberty et al. | |
| 2005/0033230 A1 | 2/2005 | Alchas et al. | |
| 2005/0038392 A1 | 2/2005 | DeSalvo | |
| 2005/0065476 A1 | 3/2005 | Jensen et al. | |
| 2005/0107740 A1 | 5/2005 | Jensen et al. | |
| 2005/0171485 A1 | 8/2005 | Larsen et al. | |
| 2006/0184133 A1 | 8/2006 | Pessin | |
| 2007/0293819 A1 | 12/2007 | Giambattista et al. | |

FOREIGN PATENT DOCUMENTS

| | | |
|---|---|---|
| EP | 0 409 180 A1 | 1/1991 |
| EP | 0 520 930 A1 | 12/1992 |
| EP | 0 555 974 A1 | 8/1993 |
| EP | 0903157 | 3/1999 |
| EP | 1448256 | 8/2004 |

(56) References Cited

FOREIGN PATENT DOCUMENTS

| EP | 1557191 | 7/2005 |
|---|---|---|
| EP | 1289587 | 8/2005 |
| FR | 2529086 | 12/1983 |
| GB | 2214082 | 8/1989 |
| JP | 3-139363 | 6/1991 |
| JP | H04501672 B2 | 3/1992 |
| JP | 5-337182 | 12/1993 |
| JP | 06-049074 A | 2/1994 |
| JP | 6-502787 | 3/1994 |
| JP | 3039310 | 9/1996 |
| JP | H08508185 A | 9/1996 |
| JP | 9-117507 | 5/1997 |
| JP | 11-137687 | 5/1999 |
| JP | 11-511364 | 10/1999 |
| JP | 2000 167052 | 6/2000 |
| JP | 2001-526095 | 12/2001 |
| JP | 2003-511105 A | 3/2003 |
| RU | 2003352 C1 | 11/1993 |
| RU | 2098143 C1 | 12/1997 |
| WO | WO 91/11212 | 8/1991 |
| WO | WO 92/19296 | 12/1992 |
| WO | WO 93/00122 | 1/1993 |
| WO | WO 93/00948 | 1/1993 |
| WO | 93/16746 A1 | 9/1993 |
| WO | WO 95/29721 | 11/1995 |
| WO | WO97/10864 | 3/1997 |
| WO | WO 97/14455 | 4/1997 |
| WO | WO 97/23253 | 7/1997 |
| WO | WO 97/39787 | 10/1997 |
| WO | WO 99/22790 | 5/1999 |
| WO | WO 99/25402 | 5/1999 |
| WO | WO 99/32177 | 7/1999 |
| WO | 0124855 A1 | 4/2001 |
| WO | WO 01/32255 | 5/2001 |
| WO | WO 01/37898 | 5/2001 |
| WO | WO 01/64270 | 9/2001 |
| WO | WO01/64271 | 9/2001 |
| WO | WO 01/76665 | 10/2001 |
| WO | 02/09797 A1 | 2/2002 |
| WO | WO 03/066141 | 8/2003 |
| WO | 2005/035029 A1 | 4/2005 |
| WO | 2005038392 A2 | 4/2005 |

OTHER PUBLICATIONS

Summons to Attend Oral Proceedings by EPO in Opposition of EP Pat. No. 1 448 256 Dated Nov. 27, 2007.
Interlocutory Decision in Opposition Proceedings in European Patent 1557191 (EP Application No. 05006983.0) Dated Jul. 29, 2011.
Becton Dickinson (BD) AutoShield Duo Needle Instructions for Use (IFU), publication date unknown, copyright 2011.
Becton Dickinson (BD) AutoShield Needle Instructions for Use (IFU), publication date unknown, copyright 2008.
Ypsomed Clickfine AutoProtect Needle Brochure, publication date unknown, cites to Jan. 2012 document.
Notice of Opposition and Response in Opposition of EP Pat. No. 1 448 256, May 3, 2006.
U.S. Appl. No. 95/000,288. (Inter Partes Reexamination of U.S. Pat. No. 6,885,129).
Diggle et al., Effect of Needle Length on Incidence of Local Reactions to Routine Immunization in Infants Aged 4 Months: Randomized Controlled Trial (Abstract) pp. 931-933, BMJ vol. 321, Oct. 14, 2000.
Unverified English Language Translation of WO 99/25402, May 27, 1999.
Decision Rejecting Opposition in EP Application No. 02 803 754.7 (Patent No. 1448256) Mailed May 30, 2008.
Minutes of Oral Proceedings Before the Opposition Division Opened on May 6, 2008 in EP Application No. 02 803 754.7 (Patent No. 1448256) Mailed May 30, 2008.
Non-Final Office Action in Inter Partes Reexamination Application No. 95/000,288 Mailed Feb. 29, 2008.
Amendment and Response by Patentee in Inter Partes Reexamination Application No. 95/000,288 Submitted Apr. 29, 2008.
3$^{rd}$ Party Comments in Inter Partes Reexamination No. 95/000,288 Submitted May 29, 2008.
Action Closing Prosecution in Inter Partes Reexamination Application No. 95/000,288 Mailed Aug. 22, 2008.
Amendment and Response by Patentee in Inter Partes Reexamination Application No. 95/000,288 Submitted Sep. 22, 2008.
3$^{rd}$ Party Comments in Inter Partes Reexamination Application No. 95/000,288 Submitted Oct. 22, 2008.
Right of Appeal Notice in Inter Partes Reexamination Application No. 95/000,288 Mailed Nov. 20, 2008.
Patent Owner Appeal Brief Mailed Mar. 9, 2009 in Inter Partes Reexamination Application No. 95/000,288.
Third Party Requestor Cross-Appeal Brief Mailed Mar. 5, 2009 in Inter Partes Reexamination Application No. 95/000,288.
Written Opinion Mailed Apr. 3, 2009 of EP Opposition of EP Patent No. 1,289,587.
Minutes of Oral Proceeding Held Feb. 10, 2009, and Mailed Apr. 2, 2009 of EP Opposition of EP Patent No. 1,289,587.
Patent Owner Respondent Brief Mailed Apr. 6, 2009 in Inter Partes Reexamination Application No. 95/000,288.
Third Party Respondent Brief Mailed Apr. 8, 2009 in Inter Partes Reexamination Application No. 95/000,288.
Machine Translation of JP 3039310, Jul. 15, 1997.
Machine Translation of JP 2000 167052, Mar. 25, 2003.
Corrected Third Party Respondent's Brief Filed Oct. 9, 2009 in Reexam No. 95/000,288, US Patent No. 6,547,764, Issue Date: Apr. 15, 2003, U.S. Appl. No. 09/870,276, filed May 30, 2010, Inventors: Larsen et al.
Examiner's Answer Mailed Nov. 17, 2009 in Reexam No. 95/000,288, US Patent No. 6,547,764, Issue Date: Apr. 15, 2003, U.S. Appl. No. 09/870,276, filed May 30, 2010, Inventors: Larsen et al.
Rebuttal Brief for Appellant/Patent Owner in Response to Examiner's Answer Filed Dec. 17, 2009 in Reexam No. 95/000,288, US Patent No. 6,547,764, Issue Date: Apr. 15, 2003, U.S. Appl. No. 09/870,276, filed May 30, 2010, Inventors: Larsen et al.
Notice of Allowance Mailed Aug. 30, 2004 for U.S. Appl. No. 10/307,054, filed Nov. 29, 2002 by Jensen et al.
Non-Final Office Action Mailed Aug. 31, 2005 for U.S. Appl. No. 10/978,760, filed Nov. 1, 2004 by Jensen et al.
Final Office Action Mailed Feb. 9, 2006 for U.S. Appl. No. 10/978,760, filed Nov. 1, 2004 by Jensen et al.
Notice of Allowance Mailed Sep. 19, 2006 for U.S. Appl. No. 10/978,760, filed Nov. 1, 2004 by Jensen et al.
Non-Final Office Action Mailed Jan. 9, 2007 for U.S. Appl. No. 10/978,760, filed Nov. 1, 2004 by Jensen et al.
Final Office Action Mailed Aug. 21, 2008 for U.S. Appl. No. 10/978,760, filed Nov. 1, 2004 by Jensen et al.
Notice of Allowance Mailed May 7, 2009 for U.S. Appl. No. 10/978,760, filed Nov. 1, 2004 by Jensen et al.
Non-Final Office Action Mailed Apr. 14, 2006 for U.S. Appl. No. 11/017,116, filed Dec. 20, 2004 by Jensen et al.
Non-Final OA Mailed Apr. 7, 2010 in U.S. Appl. No. 12/470,098, filed May 21, 2009 by Jensen et al.
Notice of Appeal and Petition Under 37 CFR 1.181 in Inter Partes Reexamination Application No. 95/000288 Mailed Dec. 22, 2008.
Office Action Mailed May 26, 2010 Regarding Third Party Requester's Non-Compliant Cross Appeal in Reexam No. 95/000288, US Patent No. 6,547,764, Issue Date: Apr. 15, 2003, U.S. Appl. No. 09/870,276, filed May 30, 2001, Inventors: Larsen et al.
English Abstract of JP 3-139363 Filed Jun. 13, 1991.
English Abstract of 5-337182 Filed Dec. 21, 1993.
Machine Translation of JP 11-137687 Filed May 25, 1999.
Order Returning Undocketed Appeal to Examiner Mailed May 20, 2010 in Reexam No. 95,000288, US Patent No. 6,547,764, Issue Date: Apr. 15, 2003, U.S. Appl. No. 09/870,276, filed May 30, 2001, Inventors: Larsen et al.

(56) References Cited

OTHER PUBLICATIONS

Decision Dismissing Patent Owner's Petition Mailed Jun. 2, 2010 in Reexam No. 95/000,288, US Patent No. 6,547,764, Issue Date: Apr. 15, 2003, U.S. Appl. No. 09/870,276, filed May 30, 2010, Inventors: Larsen et al.

Submission of Patentee Novo Nordisk in Opposition of EP Pat. No. 1 448 256 Dated Apr. 3, 2007.

Board of Patent Appeals and Interferences Decision on Appeal (Reexamination 95/000,288 of U.S. Patent No. 6,547,764) Mailed Feb. 14, 2011.

Board of Patent Appeals and Interferences Decision on Request for Rehearing (Reexamination 95/000,288 of U.S. Patent No. 6,547,764) Mailed Jul. 18, 2011.

* cited by examiner

DISPOSABLE DOUBLE POINT INJECTION NEEDLE AND AN INSULIN INJECTION SYSTEM COMPRISING A DISPOSABLE DOUBLE POINT INJECTION NEEDLE

CROSS-REFERENCE TO RELATED APPLICATIONS

This application is a continuation of U.S. application Ser. No. 11/097,414 filed Apr. 1, 2005 (allowed), which is a continuation of U.S. application Ser. No. 10/379,021 filed on Mar. 4, 2003 (Abandoned), which is a continuation of U.S. application Ser. No. 09/870,276 filed May 30, 2001 (U.S. Pat. No. 6,547,764), and claims priority under 35 U.S.C. 119 of Danish application PA 2000 01790 filed Nov. 28, 2000; European application EPO 00610052.3 filed May 31, 2000 and U.S. provisional application 60/254,051 filed Dec. 7, 2000, the contents of all of these applications are fully incorporated herein by reference.

THE TECHNICAL FIELD OF THE INVENTION

The invention relates to a disposable double pointed injection needle having an injection part with a skin piercing end and a cartridge part for inserting into a cartridge containing a liquid medicine to be injected subcutaneously. The cannula of the injection needle is fastened in a needle hub for mounting on a syringe, which syringe supports the cartridge into which the cartridge part of the injection needle penetrates.

The invention further relates to an insulin injection system comprising a pen shaped syringe supporting a cartridge with insulin, a dose setting and injection mechanism and a disposable double pointed injection needle.

DESCRIPTION OF RELATED ART

Injections where a liquid is expelled into the human body are usually performed either as intramuscular injections i.e. injections into the muscle tissue, or as subcutaneously injections i.e. injections into the subcutaneous tissue lying between the cutis and the muscle tissue.

When performing intramuscular injections of a vaccine it is according to British Medical Journal, volume 321, p. 931, important to use long injections needles in order to avoid local reactions such as redness and swelling. According to the article, use of injection needles having a length of 25 mm reduced the rate of local reaction significantly compared to an injection needle having a length of 16 mm.

Long injection needles must have a relatively large diameter in order not to break during injection. The injection needles referred to in the above mentioned article has a diameter of 23 G for the 25 mm long injection needle and 25 G for the 16 mm long injection needle.

The outside diameters of injection needles are indicated by a "G" and a gauge number increasing with thinner needles. Thus the outside diameter of a G 23 is 0.60 mm and of a G 25 0.50 mm.

It has for some years been known to provide long injection needles with safety protective devices in order to prevent accidental needle stick injuries. Such safety protective devices are e.g. known from EP 409.180 and U.S. Pat. No. 4,813,940. These known safety protective devices comprises a number of telescopic sleeves, which telescopic sleeves slides into each other in order to expose an injection needle covered by the telescopic sleeves when not in use. The injection needles used has opposite the skin piercing end a needle connector for connecting the injection needle with an ordinary hypodermic syringe. By the expression "ordinary hypodermic syringe" is meant a syringe of the type where the medicine to be injected is drawn from a vial into the syringe prior to each injection. In practical use the medicine has to flow through the injection needle twice for every injection when using such an ordinary hypodermic syringe, but due to the large diameter and the large bore of a long injection needle clogging is not a problem.

Figure 1:
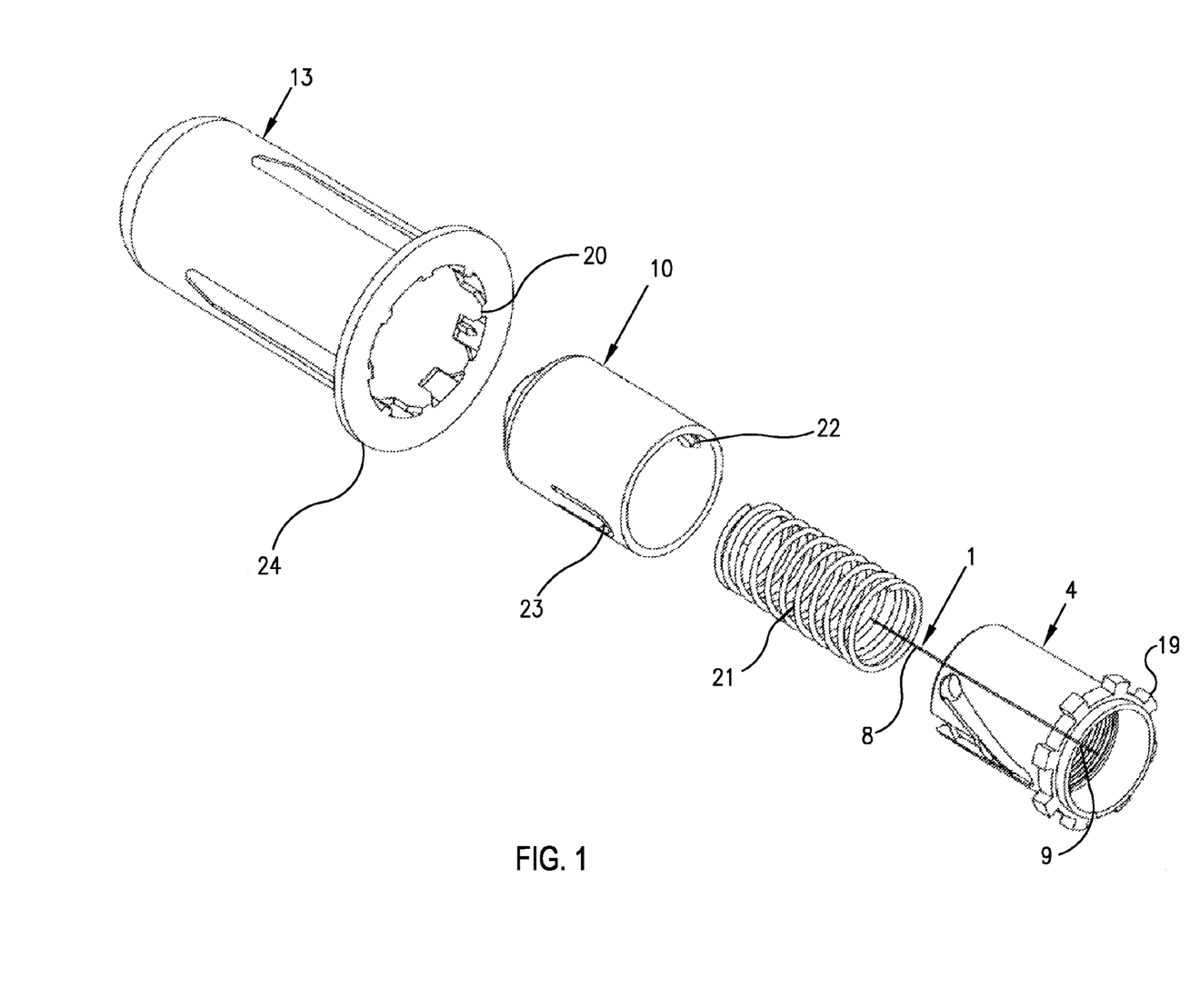
FIG. 1 Shows an exploded view of the disposable double pointed injection needle according to the invention.

U.S. Pat. No. 5,429,612 discloses yet another long injection needle having a safety protective sleeve which can be moved into a position where the safety protective sleeve covers the injection part of the needle cannula. As can be seen in FIG. 1 of U.S. Pat. No. 5,429,612 the injection part of the needle cannula has a length, which makes it necessary to support the needle cannula by at least one disk 21. The syringe is loaded with a flask containing the medicament to be injected. Since the syringe has no dose setting and injection mechanism like the ones known from insulin injection pens, the entire content of the flask is emptied into the patient in one injection, which is the usual procedure when injecting anesthesia in dentistry. When using the embodiments shown in FIGS. 2 and 3, the user must manually rotate the shield after use in order to bring the tongue 26 from the first track 23 and into the second track 24. Doing so the user is exposed to a great danger, since the rotation must be done after the contaminated needle cannula has been retracted from the body of the patient.

When providing long injection needle with safety protective sleeves there are hardly any limitation to the length of the injection needle as long as the relationship between the length and the diameter is sufficient to prevent unwanted needle breakage. The muscular tissue is in a human body normally located approximately 10 to 14 mm below the surface of the skin. The part of a long injection needle entering the human body therefore has to be at least 14 mm in order to reach into the muscular tissue of the human body. As can be seen from the prior art injection needles, the length of the needle cannula from its fastenings point in the needle connector to its skin piercing end is substantially longer than the part of the needle cannula, which enters the human body during injection. This presents however no problem since these needle has a large diameter sufficient to withstand breakage.

Some medicines however has to be injected subcutaneously i.e. in the subcutis lying between the cutis and a muscle membrane which cover the underlying muscles. If for instead insulin for treating diabetes is injected into the muscle tissue it will be absorbed in the body to quickly and an unwanted drop in the blood sugar may be the result. In order to prevent intramuscular injection of insulin it is quite common for people suffering from diabetes to inject into a lifted skin fold. It is however becoming more and more preferred by diabetic persons to inject directly at an angle of 90° without the skin fold, using an extra short needle. The extra short needle must have an overall length of the injection part of the needle cannula short enough to avoid intramuscular injections. Such extra short needles are e.g. known from WO 97.23253, which discloses an injection needle having an overall length of the injection part laying in the interval 4 to 6 mm.

Very short injection needle are not subject to breakage in the same degree as long injection needles, and can therefore be made with a much smaller diameter. WO 93.00948 reveals a short injection needle, having an injection part in the interval 8 to 12 mm, for injecting insulin. The diameter of the needle cannula is thinner than G 29. Such short and thin needles cannot be used in connection with an ordinary hypodermic syringe where the medicine is drawn up from a vial prior to each injection since this requires the medicine to flow through the needle twice for every injection, which can result in clogging of the bore of the injection needle, especially if the medicine is a suspension. However when the short and thin needle are used in connection with a syringe supporting a cartridge containing the medicine to be injected, the medicine only has to flow through the injection needle once which in itself halves the risk of clogging, and thereby allows very thin injection needles to be used. At the same time, when an injection needle has only a small diameter both outside and inside, the pressure needed to force a liquid through the bore of the injection needle is high when the injection needle is long, but substantially smaller if the injection needle is short.

DESCRIPTION OF THE INVENTION

These known short and thin injection needles are however not provided with any safety protective devices, while the safety protective sleeves known from the prior art would permanently cover a large part of the injection part of the injection needle thereby preventing a short injection needle from penetrating through the cutis layer, which layer usually is between 2 to 3 mm thick, and into the subcutis layer of a human body.

Injection needles with relatively thin diameter and with a length of the injection part of the needle cannula between 4 to 12 mm are often used for self-injection of insulin i.e. where the patient injects him or herself. However for self-injection in private settings, safety protective devices providing safety against accidental needle stick injuries are not considered to be important, since no other person beside the patient performing the self-injection has contact with the injection needle. Safety protective devices providing safety against accidental needle stick injuries would however be preferred in domestic residences if other people, and especially children, are present in the domestic residence.

It is however very important in hospital settings where many people interact to use injection needles which are provided with some kind of safety protective device preventing accidental needle stick injuries. All the prior art injection needles provided with safety protective devices are long injection needles for intramuscular injections. These long injection needles are often of the type used on traditional hypodermic syringes where the medicine has to flow through the bore of the needle twice for every injection thereby limiting the minimum diameter of the bore and the outside diameter of the injection needle. Hospitalised people suffering from diabetes are usually injected with these long injection needles having a relatively large outside diameter. This is also the case with senior citizens in retirement homes, with children in schools and in day-care facilities, in fact every place an insulin injection is performed by a professional health care worker long injection needles are used, since they are the only ones providing sufficient safety for the health care worker. The health care worker giving the injection using a long needle has to be very careful only to penetrate into the subcutis layer in order for the insulin to be correctly absorbed in the human body, and at the same time the large diameter of a long injection needle gives the patient a high pain perception. No matter how careful health care workers are when injecting insulin, the insulin will sometimes unintended be injected into the muscle tissue, with the subsequent changes in insulin absorption and diabetes control. Patients which are newly diagnosed with diabetes and not familiar with self-injection often finds a long injection needle with a large diameter very intimidating, which is also the case with children. At the same time needles with large diameters tends to fracture the skin more than thin needles.

It is an object of the present invention is to provide a short and thin disposable double pointed injection needle for subcutaneously injection, which overcomes the deficiencies of the prior art. It is further an object to provide a short and thin disposable double pointed injection needle which is equipped with a safety protective device preventing accidental needle stick injuries, and which injection needle could be used on a modern type syringe supporting a cartridge containing a liquid medicine.

This is obtained by a disposable double pointed injection needle for example, with a movable needle protector arranged on a needle hub, and which movable needle protector can be moved into, and irreversibly locked in, a position where the movable needle protector covers the skin piercing end of the injection part of the needle cannula thereby preventing needle stick injuries.

The short and thin injection needle is provided with a movable needle protector which allows normal use of the injection needle during injection, and which movable needle protector once the injection is done can be shifted manually or automatically into a position where the movable needle protector covers the skin piercing end of the needle cannula in an irreversible manner. When the skin-piercing end of the cannula is covered, the injection needle can be removed from the syringe and disposed off without endangering the people performing the injection and the people disposing of the used injection needles. The cartridge part of the needle cannula is permanently covered by the hub preventing the cartridge part of the needle cannula from accidental penetrating the skin of the persons handling the injection needle.

Hospitalised people suffering from diabetes or a similar disease is hereby provided with a disposable double pointed injection needle which only penetrates into the subcutis layer of the human body during injection and which at the same time offers sufficient protection against accidental needle sticks. This will relieve the patients from the variations in the depth of penetration occurring when injections are given using long injection needles and provide safety for the health care workers at the same time. Since the disposable double pointed injection needle is both short and thin, the pain perception will be very low.

Since especially children are very sensible to the appearance of the injection needle, a short disposable double pointed injection needle where a major part of the injection part of the needle cannula is hidden inside the boundaries of a safety shield prior to injection will make it psychologically easier for a child to accept the fact that daily injections of a liquid medicament such as insulin or growth hormone is needed.

When the movable needle protector is a cylinder-shaped safety
shield surrounding at least the major part of the injection part of the needle cannula when the needle cannula is in an unused state, and which cylinder-shaped safety shield can be longitudinal moved relatively to the needle cannula, such that the safety shield is first moved in the proximal direction when the injection part of the cannula is penetrated into the subcutis layer of a human body, thereby exposing the major part of the injection part to the human body, and which safety shield automatically moves in the distal direction until the cannula is fully surrounded by the safety shield when the injection part of said cannula is removed from the subcutis layer of a human body. it is ensured that the entire injection part of the needle cannula is securely covered at all times during the injection. In a preferred embodiment of the disposable double pointed injection needle according to the invention the safety shield is automatically moved in the distal direction when the injection part of the cannula is removed from the subcutis layer of the human body by a resilient element such as a helical spring. which resilient element is located between the needle hub and the safety shield. and which resilient element is tighten when the injection part of said cannula is penetrated into the sub-cutis layer of the human body. Such an automatic movement by a spring or another resilient element ensures that the shield is always moved into the position where its covers the injection part of the needle cannula without the need of the user to manually push the shield into this position. Any type of resilient element can be utilized, although it is preferred to use a helical spring. Such a helical spring can be either metallic or made from a polymeric material.

When the safety shield is guided on the outside surface of the needle hub, it is ensured that the safety shield can be pushed all the way back such that a major part of the injection part of the needle cannula of the injection needle is exposed to the human body during injection thereby limiting the overall length of the needle cannula of the injection needle.

When the safety shield is provided with a number of inwardly
pointed projections guided in guiding tracks provided on the external surface of the needle hub. it is ensured that the shield moves relatively to the needle cannula and the needle hub in a predetermined pattern.

In yet a preferred embodiment of the disposable double pointed injection needle according to the invention at least two guiding tracks are located opposite each other on the needle hub each comprises a first part being substantially parallel to the needle cannula and a second part being connected to the first part at an acute angle. Two, three or more guiding tracks provide stability to the shield. and an acute angle between the two parts of each track provides a smooth movement of the shield.

When one of the parts of the guiding tracks is open at the distal end of the needle hub allowing the projections to enter each guiding track, and that the open part of each guiding track at the distal end is provided with an elevation, it is ensured that the projections are easily inserted in the tracks, and that once located in the guiding tracks is prevented from sliding out of grip with the guiding track. The part of the guiding tracks being open at the distal end can either be the first part or the second part.

In another embodiment of the disposable double pointed injection needle according to the invention, each projection can be shifted between three different locations in the guidingtrack:
a first location where the safety shield surrounds at least the major part of the injection part of said cannula, and in which location said needle cannula is in an unused state
a second location where the major part of the injection part is exposed to the human body, and in which location the needle cannula is penetrated into the human body, and
a third location where the safety shield fully surrounds the injection part of the cannula, and in which location the cannula is fully removed from the human body.

By having the projections and the shield move relatively to the needle hub in the pattern, it is ensured that the major part of the needle cannula extending in the distal direction from the needle hub is inserted into the human body during injection.

When at least one of the guiding track has at least one elevation
with a steep front preventing the projection from moving backwards in the guiding track when the projection has entered the second or/and the third position, it is ensured that the safety shield can not be moved in the backward direction once an injection has commenced.

When one of the elevations is formed as a hole or a well located at the end of one of the guiding tracks near to the distal top end of the needle hub, and the projection drops into the hole or well when the projection is in the third location, such that the safety shield is irreversible locked to the needle hub when said cannula is fully removed from the human body, it is ensured that the safety shield is irreversible locked to the needle hub when the needle cannula is fully removed from the human body thereby preventing reuse of said injection needle.

When the disposable double pointed injection needle further comprises a container surrounding the needle hub. the needle cannula. the resilient element and the safety shield, and which container has inwardly pointing ribs engaging similar outwards pointing ribs on the needle hub, it is ensured that the rotational force emerging when the container is rotated is transferred to the needle hub.

It is also an object of the present invention to provide a pen based insulin injection system, which can be used in hospital settings or other public places without exposing the professional people working in these places to accidental needle stick injuries.

This is obtained by an insulin injection system having, for example, a movable needle protector arranged on a needle hub and which movable needle protector can be moved into, and irreversibly locked in, a position where the movable safety protector covers the skin piercing end of the injection part of the needle cannula thereby preventing needle stick injuries.

By having a complete system comprising both a pen shaped syringe supporting a cartridge and a short and thin safety engineered injection needle with a needle protector, a complete pen based injection system for the treatment of diabetes can now be used in hospitals only using needle-based medical devices designed to provide health care workers with additional protection against accidental needle stick injuries and potential exposure to infectious diseases.

In one embodiment of the disposable double pointed injection needle according to the invention the injection needle is further provided with means providing the user with a visual indication when the injection needle is in a potentially unsafe position. In another embodiment of the disposable double pointed injection needle according to the invention the injection needle is further provided with means providing the user with a visual indication when said disposable double pointed injection needle is in a potentially safe position. As the disposable double pointed injection needle according to the invention has previously been described it is somewhat difficult for the user to visible inspect if the disposable double pointed injection needle has been used. This problem is overcome by providing the disposable double pointed injection needle with means wherein the user is provided a visual indication when said disposable double pointed injection needle is in a potentially safe and/or unsafe position.

When the means providing the user with a visual indications comprises at least one transparent area in the movable needle protector and at least one first area and/or at least one second area located on the outside surface of the needle hub, and as disclosed in claim 16, the first areas located on the outside surface of the needle hub is visible through the transparent areas when the projection is in the first location. and/or that said second areas located on the outside surface of the needle hub is visible through the transparent areas in said movable needle protector when the projection is locked in said third location, it becomes very simple for an user to inspect whether the disposable double pointed injection needle is unused or not.

When the first areas and/or the second areas are provided with different colours or symbols, it is ensured that even users with poor sight can visible inspect whether the disposable double pointed injection needle has been used or not.

In the present context, the term 'injection' is taken to mean expelling a liquid along a hollow needle or another hollow conduit and into a human body, in which human body a part of the hollow needle or conduit is temporarily inserted.

Although the wording "human body" is used through out this application. the disposable double pointed injection needle claimed could as well be used on any mammal body without dispersing from the scope of the claims.

In the present context, the term "cartridge" is taken to mean a hollow tube-like container having one end permanently sealed by a membrane, which membrane is penetrated by the cartridge part of the needle cannula when the double pointed injection needle is attached to the cartridge or the syringe. The other end of the cartridge is a displaceable plate or cylinder that fits tightly against the inner walls of the cartridge. A discrete dose is expelled through the double pointed injection needle attached to the cartridge or the syringe if the plate or cylinder is displaced in the direction towards the permanent membrane penetrated by the cartridge part of the double pointed injection needle.

The cartridge containing the medicine is usually supported in the distal end of the housing of the syringe. The cartridge can either be permanently fastened in the housing or it can be exchangeable. If the cartridge is permanently fastened in the housing, the entire syringe is disposed of when the cartridge is empty, but if the cartridge is exchangeable then only the empty cartridge is disposed of and a new, full cartridge is loaded into the housing of the syringe.

It is to be understood that the wording "pen shaped syringe", used throughout this application, merely refers to a syringe having an oblong or elongated shape and which fits into one hand, somewhat like a pen for writing. Although such writing pens usually have a tubular cross-section, modern writing pens often have a different cross-section such as triangular, rectangular or square. Pen shaped syringes can in a similar way have a large variety of different cross-sections.

When referring to the disposable double pointed injection needle according to the present application the term "relatively thin outside diameter" is taken to mean a needle cannula having an outside diameter thinner than G28. The use of G28 needle cannulas for injecting insulin has for many years been widely accepted as the standard size, and G29 or thinner needle cannulas are therefore often referred to as "thin injection needles". The needle cannula of the disposable double pointed injection needle can be as thin as 31G or even 32G.

A "G" and a gauge number increasing with thinner needles indicate the outside diameter of the needle cannula. The following table indicates the relation between the gauge number and the outside diameter of the needle cannula, for the gauge numbers referred to in the present application.

| Gauge: | 23G | 25G | 27G | 29G | 30G | 31G | 32G |
|---|---|---|---|---|---|---|---|
| Diameter: | 0.60 mm | 0.50 mm | 0.40 mm | 0.33 mm | 0.30 mm | 0.25 mm | 0.23 mm |

The part of the needle cannula referred to as the "cartridge part" is the part entering the cartridge, which is to be understood as the part extending in the proximal direction from its fastening point in the needle hub, while the part referred to as the "injection part" of the needle cannula is the part entering the human body during injection, which is to be understood as the part extending in the proximal direction from its fastenings point in the needle hub. The injection part extending in the proximal direction from its fastening point in the needle hub is often a little longer than the part actually penetrating into the human body. The length different between the injection part and the part actually penetrating into the human body depends on the height of the hub tower and the wall thickness of the top surface of the safety shield. Usually the part of the needle cannula, which penetrates into the human body has a length between 4 to 12 mm, such that the depth of penetration lies between 4 to 12 mm.

In the present context, the term "dose setting and injection mechanism" is taken to mean a mechanism by which a desired dose of a liquid medicine contained in a cartridge can first be set and later injected, leaving the remaining part of the liquid medicine in the cartridge. The mechanism can either be mechanical or electronic, or both. The injection is usually done by having a mechanical element pressing forward the plate or cylinder inside the cartridge in correspondence with the set dose. The force used for driving forward this mechanical element is preferably delivered either physically by the user or by an electrical motor.

In the present context, the term "subcutaneously" refers to the subcutis layer of the human body, which are the layer located between the cutis and a muscle membrane covering the muscular tissue. By a number of measurements it is found that the average depth of the muscle membrane is 9.5 mm for males and 13.8 for females, measured from the outside of the human skin. Recognizing that the emission of liquid from an injection needle, due to the oblique cut end of the skin piercing end of the needle cannula, takes place in a distance from the skin piercing end in the range 0.4 to 1.2 mm, an injection needle for subcutaneously injections should preferably have an length of the part penetrating into the subcutaneous layer shorter than approximately 10 mm. Although an injection needle having a length of this part, which equals the depth of penetration, up to approximately 14 mm would be acceptable for females. In order to ensure penetration of the cutis of a human being, the minimum length of the part of the needle cannula penetrating the subcutaneous layer must be longer than approximately 4 mm.

BRIEF DESCRIPTION OF THE DRAWINGS

The invention will be explained more fully below in connection with a preferred embodiment and with reference to the drawings in which.

The figures are schematic and simplified for clarity, and they just show details, which are essential to the understanding of the invention, while other details are left out. Throughout, the same reference numerals are used for identical or corresponding parts.

DETAILED DESCRIPTION OF EMBODIMENT

Initially it may be convenient to define that, the term "distal end" of the disposable double pointed injection needle according to the invention is meant to refer to the end 2 penetrating into the human body 11, whereas the term "proximal end" is meant to refer to the opposite end 3 entering into the cartridge 12.

Figure 2:
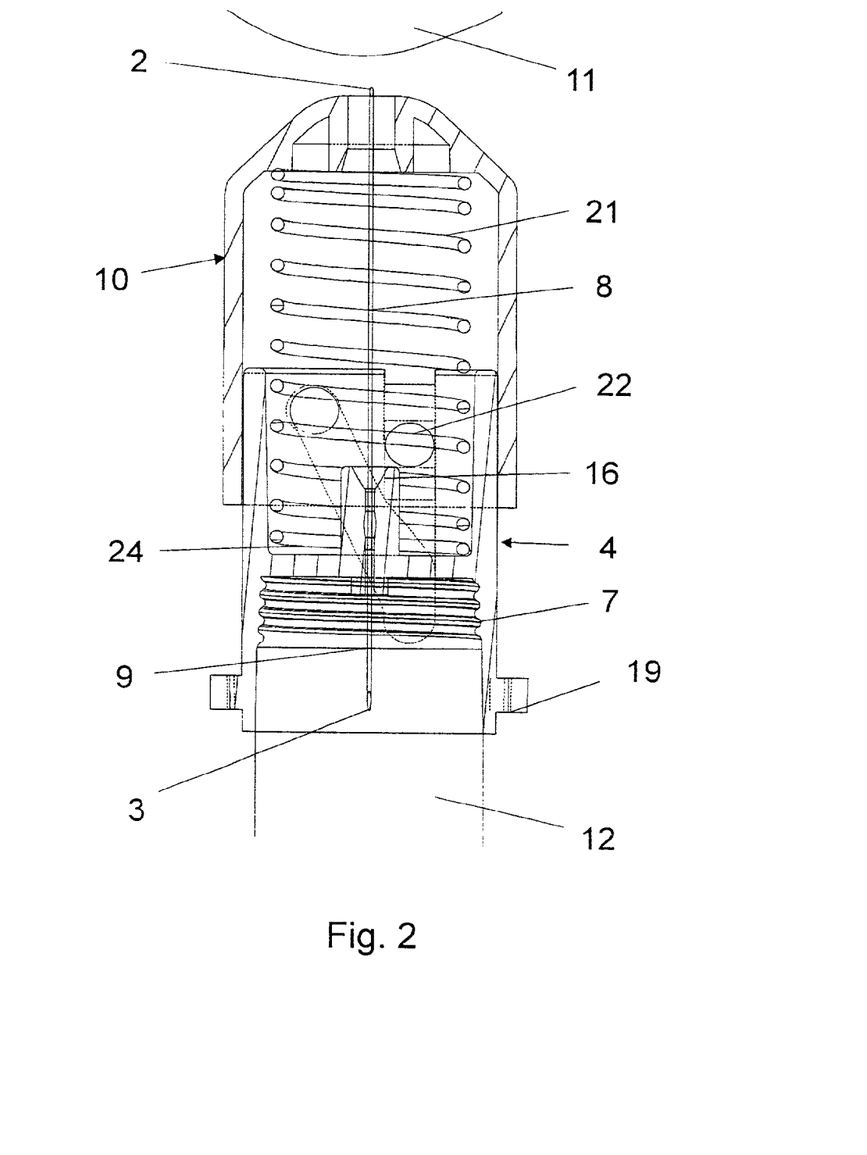
FIG. 2 Shows a sectional view of the disposable double pointed injection needle according to the invention.

FIGS. 1 and 2 shows the disposable double pointed injection needle according to the invention. The injection needle comprises of five main parts: a needle cannula 1, a needle hub 4, a safety shield 10, a resilient element 21 and a container 13.

The needle cannula 1 is elongated and both ends 2, 3 are sharpened usually by being cut in an oblique cut. The needle cannula 1 is firmly fastened in a needle hub 4. The distal part of the needle cannula 1 extending from the fastening point in the needle hub 4 is referred to as the injection part 8, and the part extending in the proximal direction from its fastening point in the needle hub 4 is referred to as the cartridge part 9.

Figure 4:
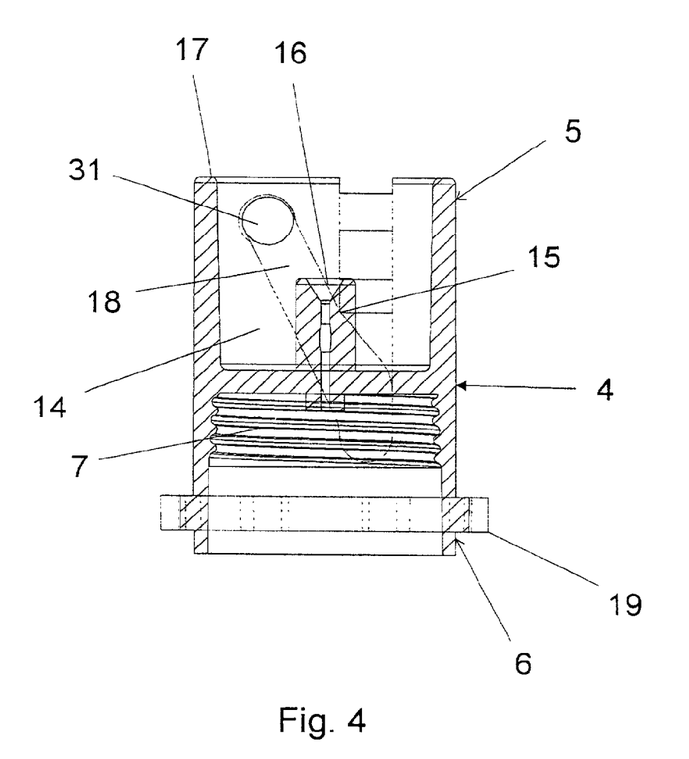
FIG. 4 Shows a sectional view of the needle hub according to an embodiment of the invention.

The needle hub 4, which is separately shown in FIG. 4, has a distal end 5 and a proximal 35 end 6. The proximal end 6 is on the interior surface provided with a thread 7, which fits over an external thread on the cartridge 12 or on a not shown syringe carrying the cartridge 12. In this way the disposable double pointed injection needle can easily be connected and disconnected to the cartridge 12 or the syringe carrying the cartridge 12. The needle hub 4 can be provided with a not shown cover covering the cartridge part 9 of the needle cannula 1. This not shown cover can be connected to the needle hub 4 by a hinge, such that the cover can be opened prior to connecting the needle hub 4 to a syringe, and closed when the needle hub 4 has been disconnected from a syringe.

The needle hub 4 has at the distal end 5 a centrally located hub tower 15 surrounded by a circular well 14 through which a channel 16 reaching all the way through the needle hub 4 to the proximal end 6 is formed. The needle cannula 1 is under manufacturing placed in this channel 16, and the channel is filled with glue or other material, which can firmly fasten the needle cannula 1 to the needle hub 4. The glue used could e.g. be ordinary glue for gluing metal to a polymeric material, or it could be glue which is harden by use of UV light. Instead of using glue, the material of the hub 4 could be melted to fasten the needle cannula 1 to the hub 4. The height of the hub tower 15 and the length of the channel 16 can vary depending on the type of the disposable double pointed injection needle. A longer channel 16 gives a better control over the sideways movements of the needle cannula 1 during manufacturing. If wanted the hub tower 15 can have a height such that the distal end of the hub tower 15 aligns the distal top surface 17 of the needle hub 4. The depth of the well 14 is chosen such that the well 14 can support a resilient element in the form of a helical spring 21 which is located between the needle hub 4 and the safety shield 10 pressing the safety shield 10 away from the needle hub 4.

The needle hub 4 is on the outside surface provided with a number of tracks 18 into which tracks 18 a number of projections 22 located on the safety shield 10 fits. At the proximal end 6, the needle hub 4 is provided with a number of outward pointing ribs 19, which interacts with a number of inwardly pointing ribs 20 located on the inside surface of the container 13.

Figure 3:
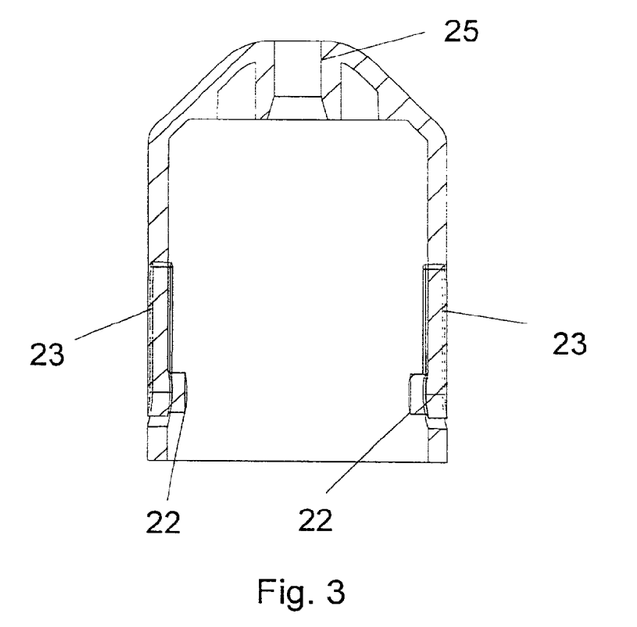
FIG. 3 Shows a sectional view of the safety shield according to an embodiment of the invention.
Figure 7:
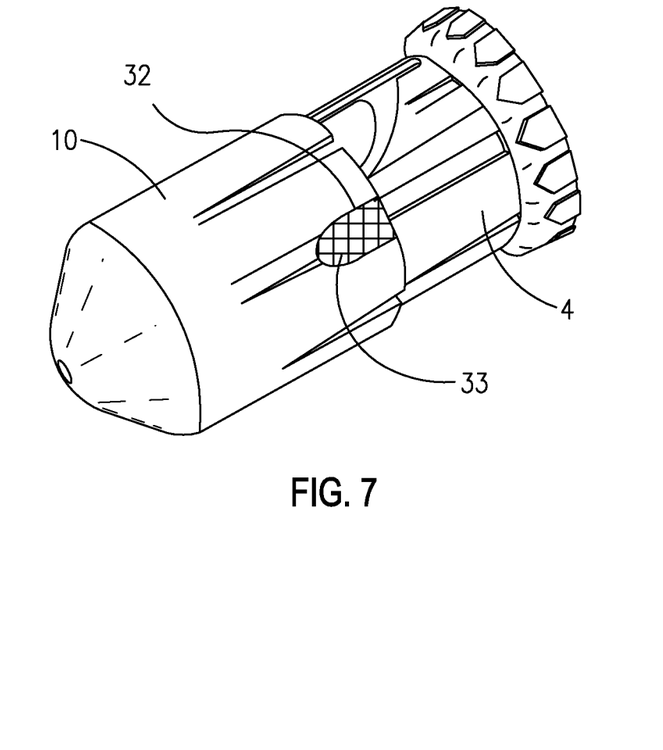
FIG. 7 Shows a perspective view of the disposable double pointed injection needle with the visual indication showing that the disposable double pointed injection needle is in an unlocked position.
Figure 8:
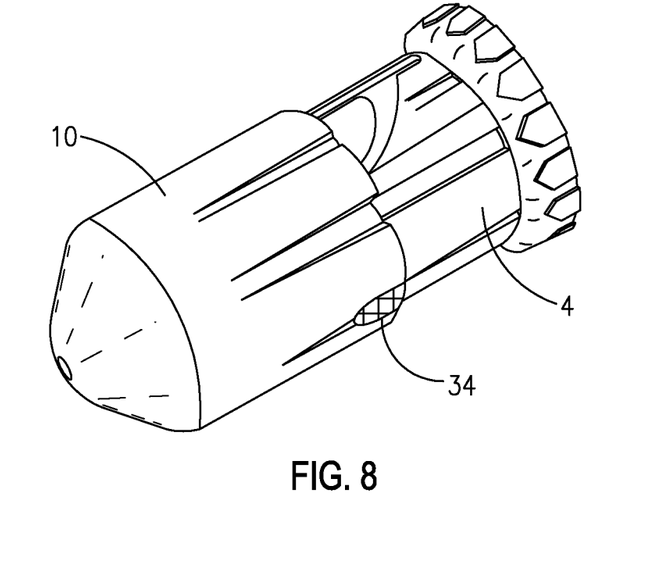
FIG. 8 Shows a perspective view of the disposable double pointed injection needle with the visual indication showing that the disposable double pointed injection needle is in a locked position.

The safety shield 10, which is shown in FIG. 3 is guided on the outside surface of the needle hub 4 as shown in FIG. 2. The safety shield 10 is on the inside surface provided with a number of inwardly pointing projections 22. Each of these projections 22 can, as shown, be carried on a resilient arm 23 formed as an integral part of the safety shield 10. The projections 22 can however be moulded directly on the inside surface of the safety shield in which case they would not be visible from outside the safety shield 10, as shown in FIG. 7 and FIG. 8. The safety shield 10 is formed as a cup or a hat and closed on all sides except the proximal side, which fits over the needle hub 4. At the distal end, the safety shield 10 is provided with a bore 25 large enough for the needle cannula 1 to pass through.

Figure 5:
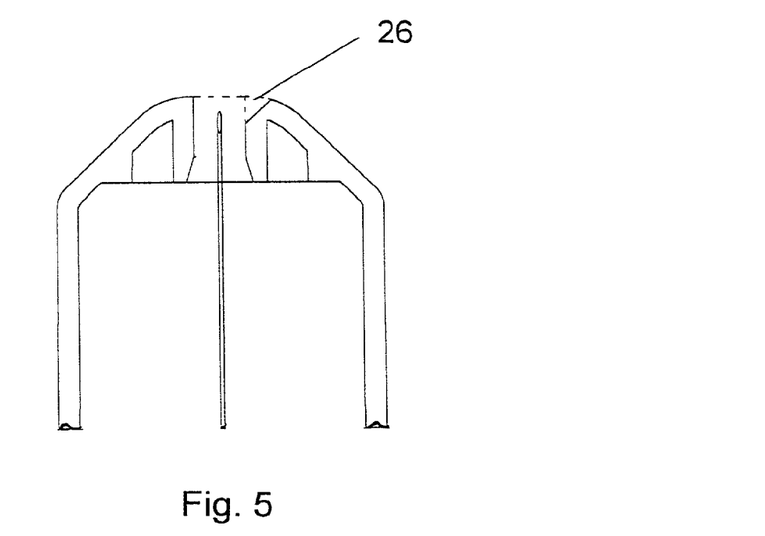
FIG. 5 Shows a sectional view of the top of the safety shield and of the skin-. piercing end of the needle cannula.

When the safety shield 10 is located on the needle hub 4 and the disposable double pointed injection needle is in its initial position, the skin-piercing end 2 of the needle cannula 1 could be located a little above the safety shield 10 as shown in FIG. 2. Prior to each injection, the user must perform a so-called air shot in order to press any air contained in the cartridge 12 out through the needle cannula 1. When doing this, it is somewhat important that the user can visibly inspect that all the air is pressed out and only fluent medicine is expelled from the needle cannula 1. Due to this the skin-piercing end 2 of the needle cannula 1 must be visible. One way of making the skin-piercing end 2 of the needle cannula 1 visible is by making the needle cannula 1 long enough to extend a little beyond the safety shield 10, although having the skin-piercing end 2 of the needle cannula 1 align the top surface of the safety shield 10 would be sufficient. Another solution could be to make the needle cannula 1 short enough to be within the boundaries of the safety shield 10 and make the safety shield 10 transparent or partly transparent. Yet another solution could be to keep the needle cannula 1 short enough to be within the boundaries of the safety shield 10 and to cut away a fraction 26 of the top of the safety shield 10 making the skin-piercing end 2 of the needle cannula 1 partly visible, as indicated with dashed lines in FIG. 5.

Figure 6:
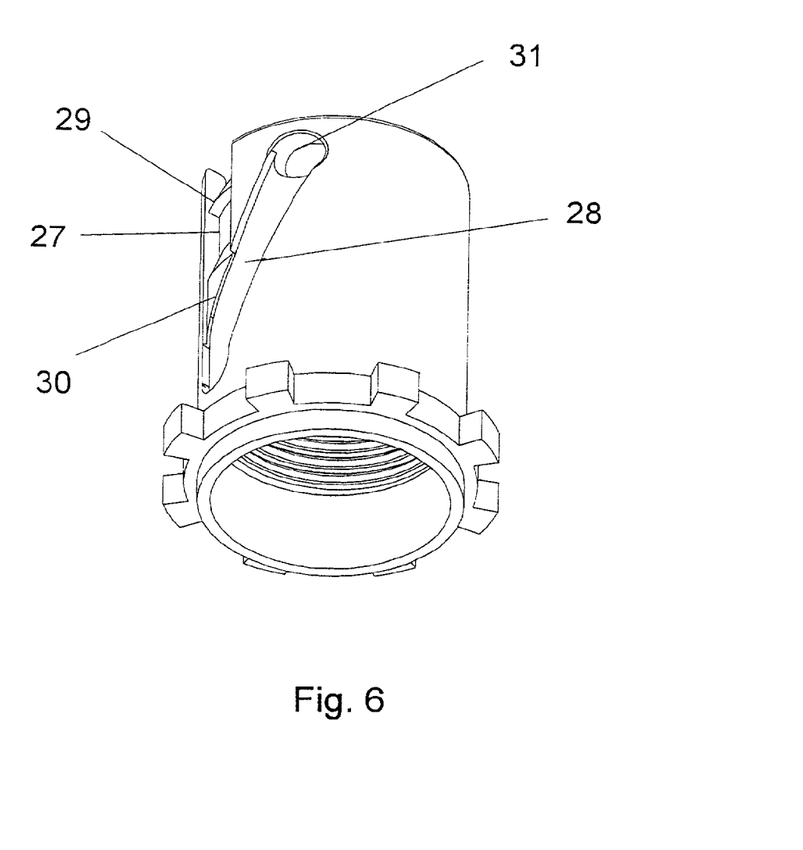
FIG. 6 Shows a perspective view of the needle hub according to an embodiment of the invention.

The hub 4 is on the outside provided with a number of tracks 18, which is best seen in FIG. 4 and in FIG. 6. Each track 18 has a first part 27 being substantially parallel to the needle cannula 1 and open at the top surface of the needle hub 4. A second part 28 of the track 18 is connected to the first part 27 at an acute angle and extends in the direction towards the distal end 5 of the needle hub 4. When the safety shield 10 is mounted over the needle hub 4, the projection 22 is passed into the first part 27 of the track 18. This first part 27 of the track 18 is provided with an elevation 29 having a sloping front allowing the projection 22 to pass over the elevation 29 and a step backside preventing the projection 22 from moving out of the track 18 once located there.

If wanted, the second part 28 of the track 18 could be the part parallel to the needle cannula 1, the first part 27 would then be connected to the second part at an acute angle. A certain degree of resiliency between the projections 22 and the tracks 18 is desired. Such a resiliency can be obtained either by providing the safety shield 10 with resilient arms 23 carrying the projections, or by making the bottom of the tracks 18 resilient e.g. by only connecting the bottom of the tracks 18 to the needle hub 4 in some areas.

During injection, as shown in FIG. 2, the safety shield 10 is pressed back against the force of the helical spring 21 by the skin of a human body 11. When the needle cannula 1 is fully inserted into the subcutaneous layer of the human body, the projection 22 enters into the second part 28 of the track 18. The two parts 27,28 of the track 18 is separated from each other by yet an elevation 30, which elevation 30 has a steep backside preventing the projection 22 form sliding back into the first part 27 of the track 18 once the projection 22 has entered into the second part 28 of the track 18. When the needle cannula 1 is removed from the subcutaneous layer of the user, the projection 22 will slide along the second part 28 of the track 18, and once the needle cannula 1 is fully retracted from the user the projection 22 will drop into a hole or well 31 where it will be permanently locked.

While commencing the injection the projection 22 is located in the first part 27 of the track 18 between the first elevation 29 and the second elevation 30, as indicated in FIG. 2, where the position of the track 18 is indicated with dashed lines. The front of the second elevation 30 has a sloping surface, which the projection 22 has to climb before entering the second part 28. The slope of this front is chosen such that the user must overcome a certain force before the projection 22 reaches the top of the elevation. For people suffering from needle anxiety it is preferred to locate the skin-piercing end 2 of the needle cannula 1 out of sight i.e. inside the boundaries of the safety shield 10, and to maximize the force a user has to apply before the safety shield 10 starts to move. Making the slope of the front of the second elevation 30 steep can maximize this force. By doing so a certain force applied by the user has to be build up before the safety shield 10 starts to move, the movement will then be rather sudden once the force is released, which is done when the projection 22 has started to be lifted over the elevation 30. The sudden release of the build up force will result in a very rapid insertion of the skin-piercing end 2 of the needle cannula 1 into the subcutaneous layer of the human body.

The most distal end of the safety shield 10 could be moulded with a textured outside surface in order to increase the friction between the skin of the human body and the surface of the safety shield 10 during injection.

When the injection needle is in the initial position ready to be inserted into the human body the safety shield 10 surrounds at least the major part of the injection part 8 of the needle cannula 1, leaving only the tip of the skin piercing end 2 of the needle cannula 1 free to be inspected when an air-shot is performed, as shown in FIG. 2. Once the needle cannula 1 is fully inserted into the human body, the major part of the injection part 8 is exposed to the human body. The only part of the injection part 8 of the needle cannula 1 not being exposed to the human body is the part lying between the fastening point in the needle hub 4 and the top surface of the safety shield 10. The length of this part depends on the height of the hub tower 15 and the wall thickness of the top surface of the safety shield 10.

In order to provide the user with a clear visible indication that the injection needle has been used, the safety shield 10 can be provided with at least one transparent area 32, which in its simplest form could be a hole in the safety shield 10. Through this transparent area 32 the user can see a first area 33 on the outside surface of the needle hub 4. Since the first part 27 of the tracks 18 is located at an acute angle to the second part 28, the safety shield 10 will rotate some degrees—depended upon the angle—relatively to the needle hub 4 when an injection is performed. This rotation will bring the transparent area 32 to a second area 34 also located on the outside surface of the needle hub 4.

If more than one transparent area 32 are provided, a corresponding numbers of first areas 33 and second areas 34 can be provided, such that a first area 33 is visible through each transparent area 32 prior to use, and that a second area 34 is visible through each transparent area 32 when the shield 10 is irreversible locked in the third position after use.

When the injection needle is in the initial position ready to be inserted into the human body, the projection 22 is located in the first part 27 of the track 18. In this position the first area 33 on the outside surface of the hub 4 is visible through the transparent area 32 of the safety shield 10. After the injection, the projection 22 is located in the hole or well 31, and the transparent area 32 of the safety shield 10 is dislocated such that the second area 34 is now visible through the transparent area 32.

Since the colour of the first area 33 indicates that the disposable double pointed injection needle is ready for use, this colour is usually green, black, blue or white. The second area 34 indicating that the disposable double pointed injection needle has been used will typically be red, orange or yellow. However it could be possible to indicate that the safety needle is in a potential unsafe position by colouring the first area 33 in a colour indicating danger, and henceforth colour the second area 34 in a colour indicating. that the safety needle is in a potentially safe position. Instead of colouring the areas 33, 34 symbols or letters indicating the state of the disposable double pointed injection needle could be used. The colours, symbols or letters can be applied to the outside surface of the needle hub using inks, coatings or mouldings. The areas 33,34 could be moulded with a depressed or textured surface in order to enhance the adherence of the colour.

The disposable double pointed injection needle is delivered ready to use either in a sterile peel bag or in a container 13. The container 13 fully houses the needle hub 4, the needle cannula 1, the helical spring 21 and the safety shield 10 before use. The proximal end of the container 13 constitutes a peripheral surface 24 onto which a not shown pealable barrier is fastened. The barrier could be a sheet made of paper or from a polymeric or metallic sheet, and is preferably glued, melted or welded on to the surface 24. The barrier is impermeable by germs such that the inside of the container is kept sterile until the barrier is broken. Although the barrier is impermeable to germs and the like, it is possible to sterilize the interior of the sheath e.g. with steam.

The proximal end of the container 13 is on the inside surface provided with a number of inwardly pointing ribs 20, which interacts with s similar number of outwardly pointing ribs 19 located on the proximal end 6 of the needle hub 4. If the fastening mechanism located on the inside surface of the needle hub 4 is a thread 7 as shown in FIG. 2, this thread 7 has to be screwed onto the thread of the cartridge 12 or the not shown syringe in order to connect these two parts. This is done by rotating the container 13 containing the disposable double pointed injection needle. When the rotational force emerging when the container 13 is rotated relatively to the cartridge 12 or the not shown syringe is transferred directly to the needle hub 4, the rotational force is prevented from damaging the tracks 18 and the projections 22.

Instead of delivering the disposable double pointed injection needle to the consumer in a separate container. the safety shield 10 itself could be used as a sterile confinement simply by prolonging the safety shield 10 in the proximal direction such that the safety shield 10 fully surrounds the needle hub 4 when the safety shield 10 is in its ready-to-use position shown in FIG. 2. The proximal end of the safety shield 10 would then have to be sealed by a pealable barrier. and the hole 25 through which the needle cannula 1 passes during injection would also have to be sealed by a pealable barrier or by a drop a soft material which can be penetrated by the needle cannula 1 e.g. silicone. The resilient arms 23 carrying the projections 22 could then be made such that the surface of the safety shield 10 was not penetrated as shown in FIG. 7 and in FIG. 8.

Some preferred embodiments have been shown in the foregoing, but it should be stressed that the invention is not limited to these, but may be embodied in other ways within the subject matter defined in the following claims.

The invention claimed is:

1. A method of preventing repeated use of a double pointed pen syringe injection needle following injecting of a patient with that needle, the method comprising:
  exposing a sharpened end of a double pointed injection needle;
  injecting a medication from a medication delivery device through the double pointed needle;
  following injecting of a patient, automatically immediately after injection providing a locking visual indication that the needle has been used and cannot be reused, thereby preventing repeated use of the double pointed needle.

2. A method of determining whether a pen syringe needle assembly having a double pointed needle cannula has been previously used, the method comprising:
  examining the needle assembly for a locking visual indicator in the form of a sheath around the needle cannula; and
  if the sheath is visible, the sheath indicates previous use of the needle assembly, thereby preventing repeated use of the needle assembly.

3. A method of determining whether a pen syringe needle assembly having a double pointed needle cannula has been previously used, the method comprising:
  examining the needle assembly for a locked visual indicator in the form of a shield
  surrounding the double pointed needle cannula; and
  if the shield surrounding the double pointed needle cannula is visible with a color
  indicator, the shield confirms that the shield is locked in place and that the pen syringe needle assembly has been previously used.

4. A method of indicating previous use of a pen syringe needle assembly having a double pointed needle, the method comprising:
  exposing a sharpened end of a double pointed needle;
  injecting a medication from a medication delivery device through the double pointed needle;
  following injecting of a patient, automatically activating a locking protective shield providing visual indication that the double pointed needle has been used, thereby minimizing inadvertent sticking of a person with the needle.

* * * * *